United States Patent [19]

Fanta et al.

[11] 4,045,387

[45] Aug. 30, 1977

[54] HIGHLY ABSORBENT POLYMERIC COMPOSITIONS DERIVED FROM FLOUR

[75] Inventors: George F. Fanta, Peoria; William M. Doane, Morton, both of Ill.

[73] Assignee: The United States of America as represented by the Secretary of Agriculture, Washington, D.C.

[21] Appl. No.: 708,792

[22] Filed: July 26, 1976

[51] Int. Cl.² ................................................ C08L 1/02
[52] U.S. Cl. ........................ 260/17.4 GC; 47/DIG. 10; 128/156; 128/284; 128/285; 128/296; 210/24; 252/316
[58] Field of Search ............................... 260/17.4 GC

[56] References Cited

U.S. PATENT DOCUMENTS

| | | | |
|---|---|---|---|
| 3,661,815 | 5/1972 | Smith | 260/17.4 GC |
| 3,935,099 | 1/1976 | Weaver et al. | 260/17.4 GC |

*Primary Examiner*—Edward M. Woodberry
*Attorney, Agent, or Firm*—M. Howard Silverstein; David G. McConnell; Curtis P. Ribando

[57] ABSTRACT

Absorbent polymeric compositions are prepared by graft polymerizing acrylonitrile onto flour or other starch-containing substrates and then subjecting the flour-polyacrylonitrile graft copolymers to alkaline saponification. Compositions prepared from gelatinized flour absorb from 1800–3000 times their weight of deionized water.

10 Claims, No Drawings

HIGHLY ABSORBENT POLYMERIC COMPOSITIONS DERIVED FROM FLOUR

BACKGROUND OF THE INVENTION

1. Field of the Invention

Our invention relates to the preparation of saponified flour-polyacrylonitrile (PAN) graft copolymer compositions which absorb up to about 3000 times their weight of deionized water and proportionately large quantities of other aqueous fluids.

2. Description of the Prior Art

Polymeric substances which have the ability to absorb aqueous fluids are known in the prior art. For example, U.S. Pat. No. 3,669,103 and 3,810,468 disclose that a variety of monomers may be polymerized, with crosslinking, to give polymeric absorbents. The crosslinking reaction is of critical importance, since the uncrosslinked polymers are water soluble and thus have no utility as absorbents.

Water-absorbing alkali metal salts of saponified granular starch-PAN graft copolymers are disclosed in U.S. Pat. No. 3,661,815. In this disclosure, starch is graft polymerized in the granule state, and the saponification is carried out in an alcohol-containing medium to obtain a granular, insoluble absorbent. U.S. Pat. No. 3,932,322 discloses a mixture of the composition of U.S. Pat. No. 3,661,815 with fumed silica or alumina. This mixture exhibits an increased rate of fluid uptake and a decreased tendency toward dusting.

Water-absorbing alkali metal salts of saponified gelatinized starch-PAN graft copolymers are disclosed in U.S. Pat. No. 3,935,099, herein incorporated by reference. In this disclosure, starch is gelatinized by heating in water prior to graft polymerization; also, the graft copolymer is saponified in water to give a viscous dispersion of highly swollen but still insoluble microgel particles. Contrary to the absorbent composition of U.S. Pat. No. 3,661,815, the composition of U.S. Pat. No. 3,935,099 may be dried to a continuous film which has an unusually high absorbency for aqueous fluids. Moreover, this film-forming tendency permits a variety of substrates to be coated with thin films of the absorbent composition and thus leads to dramatic increases in fluid absorbencies of the substrates.

SUMMARY OF THE INVENTION

The object of this invention is to prepare graft copolymer absorbents which absorb substantially larger amounts of water than those known in the prior art and to prepare these ultra-high absorbency polymers from inexpensive substrates using simple, economical procedures. We have discovered that acrylonitrile may be graft polymerized onto a relatively inexpensive flour or cereal meal and the resulting flour-PAN graft copolymer saponified with alkali to give a polymeric composition which will absorb up to about 3000 times its weight of deionized water. An absorbent composition similarly prepared from starch will absorb only about 800–900 times its weight of deionized water. These absorbent compositions are useful for reducing the water content of emulsions and dispersions, for coating substrates to increase their water-holding capacity, for the solidification of liquid wastes, and as thickening agents for aqueous systems.

DETAILED DESCRIPTION OF THE INVENTION

Flours, which are milled from the common cereal grains, such as corn and wheat, typically contain about 85% starch and 10% protein, the remainder being made up of fat, fiber, and ash. Since flour is composed mostly of starch, it might be expected that the chemical behavior of flour would be quite similar to that of starch.

It is well known that unmodified starch in the granule state is insoluble in water at ambient temperatures. It is also known that when a water suspension of unmodified granular starch is heated, the starch granules reversibly take up water with limited swelling and then, at a definite temperature, typically about 70° C., the granules undergo irreversibly a sudden rapid swelling. As the temperature is increased beyond about 70° C., the granules become more swollen and disrupted, and a higher percentage of starch is solubilized until, at a temperature of about 80°–100° C., a smooth, viscous dispersion is obtained. Starch in this form will be referred to as gelatinized. Since flour contains mostly starch, we will apply the terms "granular" and "gelatinized" to flour also. During gelatinization of flour, the protein component is also partially dissolved. The term soluble as incorporated in terms such as "water-soluble," "water-insoluble," "solubilized," etc., as used throughout the disclosure, is defined herein to include the state of being apparently soluble or highly dispersed.

Any starch-containing flour may be employed as a substrate in the instant invention. It may be granular or gelatinized, bleached or unbleached, whole (full-fat) or defatted. Preferred are the flours containing in excess of 75% starch, and particularly the cereal grain flours. The gelatinized flours yield products having absorbencies superior to the products derived from their granular counterparts. Cereal meals are also useful in the invention, and it will be understood throughout the disclosure that they are equivalent to the flours and can be substituted therefor. Exemplary substrates, without limitation thereto, are yellow corn flour, bleached pregelatinized corn flour, soft wheat flour, and whole ground corn meal.

Polyacrylonitrile (PAN) containing starch graft copolymers are well known in the prior art, and the various methods used to synthesize these graft copolymers have been reviewed by Fanta, *Block and Graft Copolymerization*, R. J. Ceresa, ed., John Wiley and Sons, 1973, Chapter 1. In this review, the influence of such variables as type of initiator used, type of pretreatment of starch, kinds of polymerization media employed, amounts of monomer used, and the like on starch graft copolymer compositions are considered. Graft copolymers prepared from proteins are also known in the prior art [Wall et al., J. Polym. Sci. C, 24: 159 (1968)]. Moreover, the procedures, reaction conditions, materials, and proportions of the polymerization, saponification, and isolation steps employed in U.S. Pat. No. 3,935,099 are applicable to the instant invention, except that flour is now substituted for the starch. These steps of preparation are briefly described below.

Although acrylonitrile (AN) is the preferred monomer, it is understood that methacrylonitrile is equivalent to the acrylonitrile monomer specified in the claims. The preferred weight ratio of flour to PAN is in the range 60:40 to 40:60; however, it is understood that graft copolymers with ratios outside this range as high as 75:25 and as low as 25:75 would also function as absorbents and would also show the desirable properties claimed in the instant invention, although perhaps to different extents. The polymerization product will hereafter be referred to as a starch-containing substrate-polyacrylonitrile graft copolymer, or simply SCS-PAN.

The preferred polymerization initiator is a ceric ammonium nitrate-nitric acid system. However, other suitable initiating systems, such as the ferrous sulfate-hydrogen peroxide redox system, cobalt-60 irradiation, or ozone will be known to those skilled in the art.

Saponification of the SCS-PAN graft copolymer is carried out in water with any alkali metal hydroxide, preferably sodium hydroxide or potassium hydroxide. It would also be obvious to use ammonium hydroxide, preferably in combination with an alkali metal hydroxide. The preferred mole ratio of alkali to AN repeating unit in PAN is in the range 0.6:1 to 1:1, although mole ratios within the range of 0.1:1 to 7.2:1 would also cause saponification to take place. Saponifications are preferably carried out in water, although it is obvious that water-containing mixtures, such as ethanol-water, can also be used. The graft copolymer is contacted with an aqueous solution of alkali metal hydroxide from 1 to 3 hr. at a temperature of 90°-100° C. Higher temperatures can also be used, if saponifications are run in pressure vessels. Saponification converts the nitrile substituents of PAN to a mixture of carboxamide and alkali metal carboxylate, the ratio of which is typically on the order of 1:2 but may vary with conditions. The saponified graft copolymer (SCS-HPAN) is water soluble in a pH range from about 5 to about 12.

Although the absorbent compositions cited in the examples are isolated by dialysis followed by drying to a film at room temperature, it is obvious that any of the isolation methods known in the prior art including those in U.S. Pat. No. 3,935,099 may be used. These methods include alcohol precipitation, drum drying, freeze drying, spray drying, and flash drying. The dried SCS-HPAN is water insoluble and has a moisture content preferably in the range of about 1 to 15% by weight.

Absorbent saponified starch-PAN graft copolymer compositions known in the prior art typically have absorbency values for deionized water on the order of 800-1000 g. per gram of polymer, when the starch is gelatinized before graft polymerization. We have confirmed this range by preparing a control composition from gelatinized starch in accordance with U.S. Pat. No. 3,935,099 by following the procedure of Example 1 of the instant application, and substituting starch for the flour. The starch-PAN graft copolymer displayed an absorbency value of 820 (Table I). Absorbent saponified starch-PAN graft copolymer compositions prepared from granular starch by the same procedure typically absorb about 300 g. of water per gram of polymer (Table I).

Water absorbencies higher than 1000 g. per gram of polymer have been obtained from gelatinized starch graft copolymer only by using special and often complex techniques. For example, U.S. Pat. No. 3,935,099 describes a saponified starch-PAN graft copolymer composition which was isolated, purified, and dried in the carboxylic acid form and then packed loosely into a column. When gaseous ammonia was passed up the column, the composition was converted to the ammonium carboxylate form, which absorbed 1300 g. of water and 80 g. of synthetic urine per gram of polymer.

U.S. Pat. No. 3,935,099 also describes a saponified starch-PAN graft copolymer composition which was dispersed in water at a concentration of 1% solids, sonified at 20K Hz for about 1 hr. to reduce viscosity from 30,000 cp. to 30 cp., and finally allowed to dry to a film. When the film was heated in a vacuum oven for 30 min. at 160° C., an absorbent composition was obtained which absorbed 2000 g. of deionized water per gram of polymer.

In view of the difficult and involved techniques used to prepare these ultra-high absorbent compositions, we were surprised to discover that absorbencies for deionized water at least as high as about 2700 g., and up to as high as about 3000 g., per gram of polymer could be easily obtained by simply substituting gelatinized flour for gelatinized starch in the graft polymerization reaction. We were also surprised to find that granular yellow corn flour produced an absorbent composition that absorbed 900 g. of water per gram of polymer, as compared with 300 g. per gram for a similarly prepared composition derived from corn starch. Properties of the instant absorbent compositions are summarized in Table I.

Since protein is the second most abundant component of flour, it was logical to assume that the ultra-high absorbencies observed were due to graft polymerization onto the protein constituent followed by alkaline saponification. However, when we attempted to graft polymerize AN onto a sample of wheat gluten, no graft polymerization was observed under the reaction conditions we used to prepare graft copolymers of flour. Moreover, treatment of the unreacted gluten, which was isolated from the grafting reaction, with sodium hydroxide under the same conditions used to saponify flour-PAN graft copolymers produced a product with negligible absorbency.

The failure to prepare an absorbent composition from protein, which comprises about 10% of the flour, and the diminished absorbency of a composition derived from starch, which comprises about 85% of the flour, prove that the ultra-high absorbencies of the instant compositions are not simply the sums of the absorbencies of the compositions derived from the two major flour components. The observed ultra-high absorbencies are thus unexpected and unpredictable from the prior art.

An important application for these absorbent polymer compositions is the reduction of the water content of emulsions, suspensions, and dispersions. For example, when a sample of skim milk containing 9.9% solids was mixed with 1%, by weight, of absorbent and the mixture let stand for 30 min. and then screened to remove water-swollen absorbent polymer, the solids content of the unabsorbed liquid was increased to 13.3%.

Another important application is the coating of various substrates to increase their water-holding capacity. For example when 1%, by weight, of absorbent polymer was dried down onto a sample of sand, a 5-g. sample of the coated sand absorbed 4.65 g. of water, as compared with 1.26 g. of water for 5 g. of uncoated sand.

Another application for these absorbent polymers is the solidification of sewage sludge and other waste materials to facilitate handling and drying. For example, when municipal sewage sludge, which contained 1.45% solids was mixed with absorbent polymer at a concentration of 1.65 parts of polymer per 100 parts of sludge, the sludge was solidified to a mass which could be easily trucked or otherwise transported without pumping.

Another application for these absorbent polymers is as thickening agents for aqueous systems. Although films or particles of these absorbent compositions retain their integrity as they swell and imbibe water, it is obvious that a film or particle which has imbibed up to 3000 times its weight of water will possess little strength and will therefore be more easily reduced to a desirably smooth dispersion than another film or particle which has absorbed only a few hundred times its weight of water. The ultra-high absorbency products of the instant invention are thus particularly well suited for use as thickeners. Moreover, since the absorbent polymer compositions swell rapidly but do not actually dissolve, they do not show the undesirable tendency to form surface-hydrated lumps or "gumballs," which is so prevalent in prior art thickeners.

Other uses disclosed in U.S. Pat. No. 3,935,099 for saponified starch-PAN, such as the entrapment and immobilization of enzymes, are anticipated for the absorbent polymers of the instant application. There are also numerous other applications for these flour graft copolymer absorbents which are not specifically listed but which will be obvious to those skilled in the art.

The following examples are intended only to further illustrate the invention and are not intended to limit the scope of the invention which is defined by the claims.

EXAMPLE 1

A. A 500-ml. resin flask was charged with 10.0 g. (dry basis) of yellow corn flour (moisture content: 12.2%) and 167 ml. of water. The stirred slurry was heated on a steam bath for 30 min. at 85° C. to effect gelatinization while a slow stream of nitrogen was allowed to bubble through the dispersion. The dispersion was cooled to 25° C. and 15.0 g. of acrylonitrile was added followed after about 30 sec. by a solution of 0.338 g. of ceric ammonium nitrate dissolved in 3 ml. of 1N nitric acid. The reaction mixture was stirred under nitrogen for 2 hr. at 25°-27° C., while controlling the exotherm with an ice bath. Dilute sodium hydroxide was added to give a pH of 7, and 200 ml. of ethanol was added. The graft copolymer was removed by filtration, washed with ethanol, and dried overnight in a vacuum oven at 60° C. The yield was 21.2 g., which corresponds to a 52.8% add-on.

B. A mixture of 1.0 g. of graft copolymer and 20 ml. of 0.5N sodium hydroxide in a 125 ml. Erlenmeyer flask was heated for 10-15 min. on a steam bath until the mixture assumed a red color and thickened enough to preclude settling on standing. The flask was then placed in a 95°-100° C. oven for 2 hr. The light yellow reaction mixture was diluted with about 400 ml. of water and dialyzed against distilled water until the pH of the dispersion was 7.1. The dispersion was then poured onto a "Teflon" tray and dried to a thin film in a forced air oven at 30°-35° C.

C. A 1.2-mg. portion of the air-dried film was accurately weighed and added to 50 ml. of deionized water. The mixture was allowed to stand for 30 min. and the swollen polymer was then separated from excess water by screening through a tared 325 mesh sieve which was 4.8 cm. in diameter. The polymer on the sieve was allowed to drain for 20-30 min., and the sieve was weighed to determine the weight of water-swollen gel (3.17 g.). An absorbency of 2640 g. of water per gram of polymer was calculated (Table I).

A 74.9-mg. portion of the air-dried film was added to 50 ml. of a synthetic urine solution prepared from 0.64 g. of $CaCl_2$, 1.14 g. of $MgSO_4.7H_2O$, 8.20 g. of NaCl, 20.0 g. of urea, and 1000 ml. of water. The mixture was allowed to stand for 30 min., screened through the 325 mesh sieve, and allowed to drain for 10 min. A synthetic urine absorbency of 57 g. per gram of polymer was calculated from the weight of swollen polymer retained on the sieve (Table I).

EXAMPLE 2

A 500-ml. resin flask was charged with 10.0 g. (dry basis) of granular yellow corn flour (moisture content: 12.2%) and 167 ml. of water, and the stirred slurry was purged with a slow stream of nitrogen at 25° C. for 1 hr. Acrylonitrile (15.0 g.) was added followed after about 30 sec. by a solution of 0.338 g. of ceric ammonium nitrate in 3 ml. of 1N nitric acid. The reaction mixture was stirred under nitrogen for 2 hr. at 25°-27° C., while controlling the exotherm with an ice bath, and was then worked up as in Example 1A. The yield of graft copolymer was 16.7 g., which corresponds to a 40.1% add-on.

Saponification of the graft copolymer with sodium hydroxide was carried out as in Example 1B. When tested by a method similar to that of Example 1C, the saponified graft copolymer absorbed 900 g. of water and 32 g. of synthetic urine per gram of polymer (Table I).

EXAMPLE 3

The procedure was that of Example 2, with the exception that a bleached pregelatinized corn flour (moisture content: 8.25%) was used. The yield of graft copolymer was 23.5 g., which corresponds to a 57.5% add-on.

Saponification of the graft copolymer was carried out as in Example 1B. When tested by a method similar to that of Example 1C, the saponified graft copolymer absorbed 2670 g. of water and 76 g. of synthetic urine per gram of polymer (Table I).

EXAMPLE 4

The procedure was that of Example 1, with the exception that soft wheat flour (moisture content: 14.9%) was used. The yield of graft copolymer was 21.0 g., which corresponds to a 52.3% add-on.

Saponification of the graft copolymer was carried out as in Example 1B. When tested by a method similar to that of Example 1C, the saponified graft copolymer absorbed 2060 g. of water and 44 g. of synthetic urine per gram of polymer (Table I).

EXAMPLE 5

A 500 -ml. resin flask was charged with 10.0 g. (dry basis) of whole ground corn meal (moisture content: 8.4%) and 167 ml. of water, and the slurry was heated to 85° C. and cooled to 25° C. as in Example 1. Acrylonitrile (15.0 g.) was added followed after about 30 sec. by a solution of 0.338 g. of ceric ammonium nitrate in 3 ml. of 1N nitric acid. Since there was no apparent reaction after stirring for 30 min. at 25° C., a second 0.338-g. portion of ceric ammonium nitrate in 3 ml. of 1N nitric acid was added. An exothermic reaction now took place. The mixture was stirred under nitrogen for an additional 1.5 hr. at 25°-27° C. and the graft copolymer isolated as in Example 1. The yield of graft copolymer was 17.2 g., which corresponds to a 41.8% add-on.

Saponification of the graft copolymer was carried out as in Example 1B. When tested by a method similar to that of Example 1C, the saponified graft copolymer absorbed 1890 g. of water and 39 g. of synthetic urine per gram of polymer (Table I).

EXAMPLE 6

A 500-ml. resin flask was charged with 10.0 g. (dry basis) of wheat gluten (moisture content: 7.0%) and 167 ml. of water, and the slurry was heated to 85° C. and cooled to 25° C. as in Example 1. Acrylonitrile (15.0 g.) was added followed after about 1 min. by a solution of 0.338 g. of ceric ammonium nitrate in 3 ml. of 1N nitric acid. After the mixture had stirred for 15–20 min. with no apparent reaction, 1N nitric acid was added to adjust the pH from 2.6 to 1.9, and a second 0.338-g. portion of ceric ammonium nitrate in 3 ml. of 1N nitric acid was added. After the mixture had stirred an additional 1 hr. and 40 min. with no apparent reaction, the reaction product was isolated as in Example 1. The yield was 9.4 g. of apparently unreacted wheat gluten. Infrared analysis showed no nitrile absorption.

A 1.0-g. portion of the unreacted wheat gluten was treated with sodium hydroxide under the saponification conditions described in Example 1B. When tested by a method similar to Example 1C, the dried alkali-treated wheat gluten absorbed a negligible amount of water.

EXAMPLE 7

This example shows the utility of the instant absorbent polymers for the coating of various substrates to increase their water-holding capacity.

Table I

| Test | Substrate | Pretreatment | % Add-on | Absorbency of saponified product, g./g. | |
|---|---|---|---|---|---|
| | | | | Water | Synthetic urine |
| Control | Corn starch (control) | Gelatinized at 85° C. | 59 | 820 | 40 |
| Control | Corn starch (control) | Granular | 55 | 298 | 28 |
| Example 1 | Yellow corn flour | Gelatinized at 85° C. | 53 | 2640 | 57 |
| Example 2 | Yellow corn flour | Granular | 40 | 900 | 32 |
| Example 3 | Bleached pregelatinized corn flour | Not further cooked | 58 | 2670 | 76 |
| Example 4 | Soft wheat flour | Gelatinized at 85° C. | 52 | 2060 | 44 |
| Example 5 | Whole ground corn meal | Gelatinized at 85° C. | 42 | 1890 | 39 |

A dispersion of 0.10 g. of the absorbent polymer composition of Example 1B in 10 ml. of water was prepared, and 10.0 g. of sand was mixed into the viscous dispersion. The resulting mixture was allowed to air dry. A 5.0-g. portion of the coated sand was weighed into a small beaker, and deionized water was added until no more water was absorbed. The amount of water absorbed by the coated sand was 4.65 g., as compared with 1.26 g. of water for a 5.0-g. sample of uncoated sand.

EXAMPLE 8

This example shows the utility of the instant absorbent polymers for concentrating aqueous emulsions or dispersions.

A 10-ml. sample of skim milk containing 9.9% solids was mixed with 0.10 g. of the absorbent polymer composition of Example 1B and the mixture allowed to stand for 30 min. Unabsorbed liquid was separated by screening through a 325 mesh sieve. The unabsorbed liquid contained 13.3% solids.

EXAMPLE 9

This example illustrates the utility of the instant absorbent polymers for solidifying sewage sludge and other waste materials to facilitate handling.

The absorbent polymer composition of Example 1B was added portionwise to a weighed sample of municipal sewage sludge which contained 1.45% solids and had a pH of 6.7. At a concentration of 1.65 parts of absorbent polymer per 100 parts of sludge, by weight, the sludge was solidified to a heavy-bodied, gelatinous mass which could be easily trucked or otherwise transported without pumping.

EXAMPLE 10

This example illustrates the utility of the instant absorbent polymers as thickening agents for aqueous systems.

A smooth 1% dispersion of the absorbent composition of Example 5 was prepared by adding 0.50 g. of polymer to 50 ml. of water and stirring the mixture gently with a spatula. Brookfield viscosity of the dispersion was 1840 cp. at 12 r.p.m. and 1400 cp. at 30 r.p.m.

It is to be understood that the foregoing detailed description is given by way of illustration and that modification and variations may be made therein without departing from the spirit and scope of the invention.

We claim:

1. A method of preparing water-insoluble, aqueous fluid-absorbing compositions comprising the following steps:

a. graft polymerizing acrylontrile onto a starch-containing substrate to form a starch-containing substrate-polyacrylonitrile (SCS-PAN) graft copolymer, wherein said starch-containing substrate is selected from the group consisting of flours and meals, and wherein the weight ratio of said substrate to said acrylonitrile is in the range of 75:25 to 25:75;

b. saponifying the SCS-PAN graft copolymer from step (a) in an aqueous slurry with an alkali in amounts such that the molar ratio of alkali to the acrylonitrile repeating unit of said SCS-PAN graft copolymer is from about 0.1:1 to about 7:1 to form a water-soluble saponified graft copolymer (SCS-HPAN); and c. drying said water-soluble SCS-HPAN from step (b) to a moisture level in the range of about 1 to 15% water by weight, whereby said SCS-HPAN is rendered water-insoluble.

2. The method as defined in claim 1 wherein the weight ratio of said starch-containing substrate to said acrylonitrile is in the range of 60:40 to 40:60.

3. The method as defined in claim 1 wherein said starch-containing substrate selected from the group consisting of flours and meals comprises granular starch.

4. The method as defined in claim 1 wherein said starch-containing substrate selected from the group consisting of flours and meals comprises gelatinized starch.

5. The method as defined in claim 1 wherein said starch-containing substrate is selected from the group consisting of yellow corn flour, bleached pregelatinized corn flour, soft wheat flour, and whole ground corn meal.

6. Aqueous fluid-absorbing compositions comprising water-insoluble alkali salts of saponified starch-containing substrate-polyacrylonitrile (SCS-HPAN) graft copolymers, wherein said starch-containing substrate is selected from the group consisting of flours and meals, and wherein the weight ratio of said substrate to said acrylonitrile is in the range of 75:25 to 25:75, said SCS-HPAN graft copolymers being further characterized as water-insoluble solids capable of absorbing up to about 3000 parts of water by weight per part of said water-insoluble solids.

7. The composition as defined in claim 6 wherein the weight ratio of said starch-containing substrate to said acrylonitrile is in the range of 60:40 to 40:60.

8. The composition as defined in claim 6 wherein said starch-containing substrate selected from the group consisting of flours and meals comprises granular starch.

9. The composition as defined in claim 6 wherein said starch-containing substrate selected from the group consisting of flours and meals. comprises gelatinized starch.

10. The composition as defined in claim 6 wherein said starch-containing substrate is selected from the group consisting of yellow corn flour, bleached pregelatinized corn flour, soft wheat flour, and whole ground corn meal.

* * * * *